US00PP24320P2

(12) United States Plant Patent
Sato et al.

(10) Patent No.: US PP24,320 P2
(45) Date of Patent: Mar. 18, 2014

(54) **NEW GUINEA *IMPATIENS* PLANT NAMED 'SAKIMP027'**

(50) Latin Name: ***Impatiens hybrida* hort**
Varietal Denomination: SAKIMP027

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 13/694,832

(22) Filed: Jan. 9, 2013

(51) Int. Cl.
*A01H 5/00* (2006.01)

(52) U.S. Cl.
USPC ..... Plt./318.2

(58) Field of Classification Search
USPC ..... Plt./318.1, 318.2, 317
See application file for complete search history.

*Primary Examiner* — Howard Locker
(74) *Attorney, Agent, or Firm* — Barbara Campbell; Cochran Freund & Young LLC

(57) ABSTRACT

A New Guinea *Impatiens* plant particularly distinguished by having a white flower color, strong root system and a compact plant growth habit, is disclosed.

1 Drawing Sheet

Genus and species: *Impatiens hybrida* hort.
Variety denomination: 'SAKIMP027'.

BACKGROUND OF THE NEW PLANT

The present invention comprises of a new and distinct cultivar of New Guinea *Impatiens*, botanically known as *Impatiens hybrida* hort, and referred to by the variety name 'SAKIMP027'. *Impatiens* variety 'SAKIMP027' originated from a hybridization in Misato, Japan between the female *Impatiens* line 'NE-4391', an unpatented proprietary *Impatiens* breeding line with a white flower color and the male *Impatiens* line 'H-10UA', an unpatented proprietary *Impatiens* breeding line with a white flower color.

In October 2008, the female parent line 'NE-4391' and the male parent line 'H-10UA' were crossed and a population of $F_1$ plants was created. The $F_1$ plants were evaluated in Misato, Japan in an open field trial. The criteria for plant selection included a beautiful white flower color, strong root system and a compact plant growth habit. At the completion of the trial, one single-plant selection was made based on the aforementioned criteria and vegetatively propagated. From May to August 2010, the selection was evaluated in an open field in Misato, Japan. The selection subsequently was named 'SAKIMP027'. The selection has been asexually propagated by means of vegetative cuttings at Salinas, Calif., and has been found to retain all of its unique characteristics and reproduce true to type in successive generations though such vegetative propagation.

SUMMARY

The following are the most outstanding and distinguishing characteristics of this new variety when grown under normal horticultural practices in Salinas, Calif.

1. White flower color;
2. Strong root system; and
3. A compact plant growth habit.

DESCRIPTION OF THE PHOTOGRAPHS

This *Impatiens* plant is illustrated by the accompanying photographs which show the plant's overall plant habit including form, foliage, and flowers. The photographs are of a four-month-old plant grown in Salinas, Calif. under greenhouse conditions in the spring of 2012. The colors shown are as true as can be reasonably obtained by conventional photographic procedures.

DESCRIPTION OF THE NEW VARIETY

Figure 1:
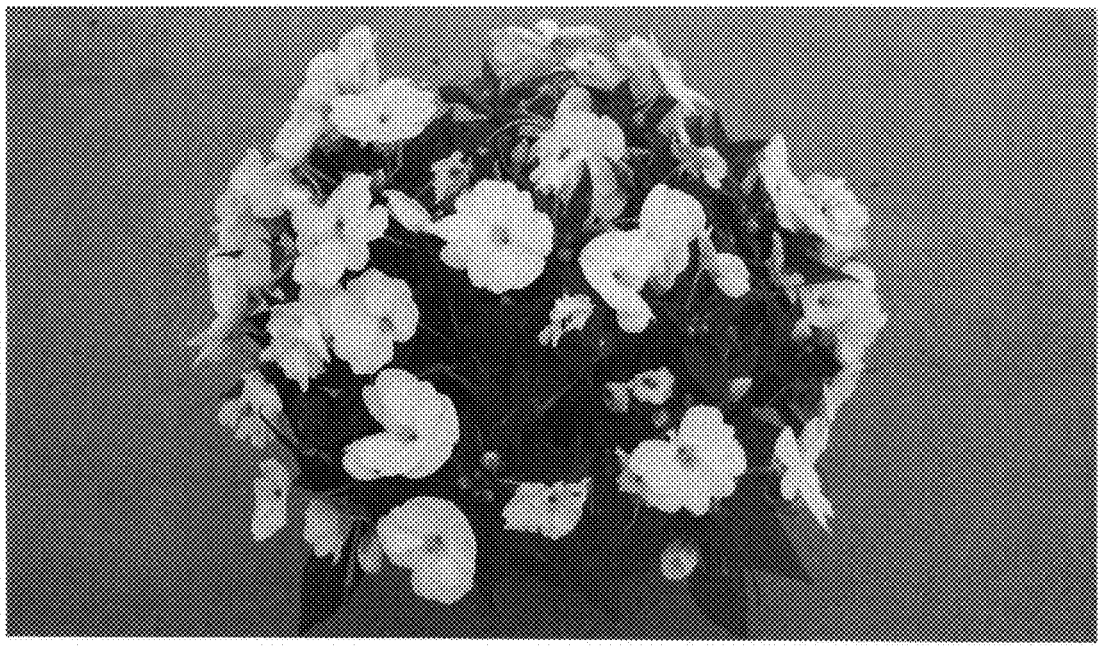
FIG. 1 shows the overall plant habit of the plant grown in a pot.
Figure 2:
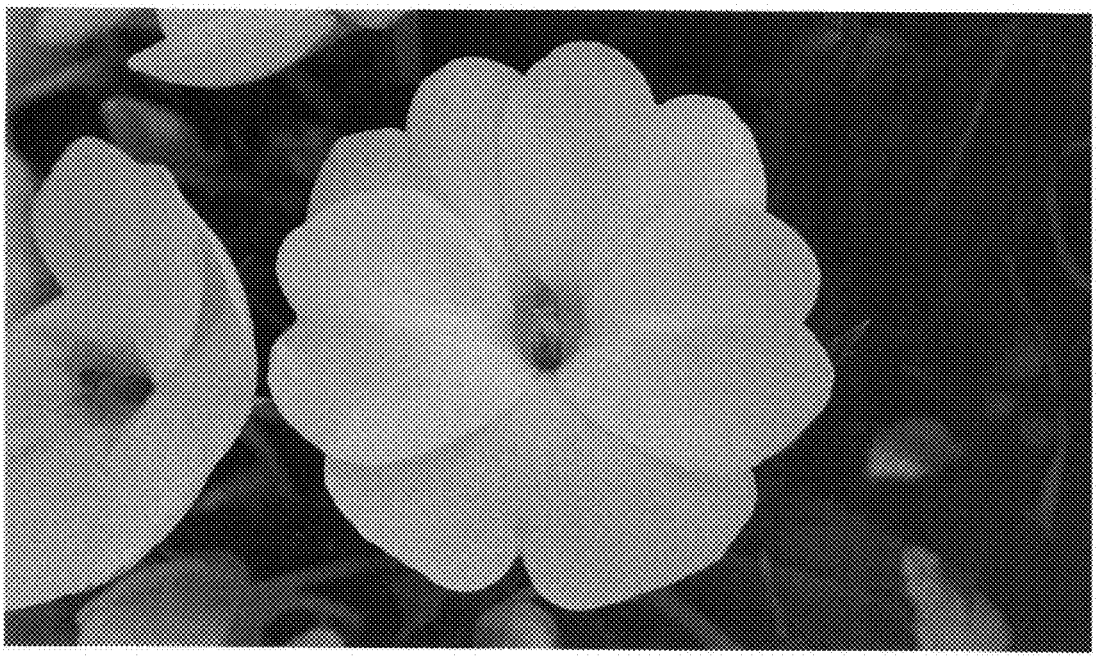
FIG. 2 shows a close-up of the mature inflorescence of the plant.

The following detailed descriptions set forth the distinctive characteristics of 'SAKIMP027'. The data which define these characteristics were collected from asexual reproductions carried out in Salinas, Calif. Data was collected on four-month-old plants grown under greenhouse conditions in Salinas, Calif. in the summer of 2012. Color references are to The R.H.S. Colour Chart of The Royal Horticultural Society of London (R.H.S.), 4$^{th}$ edition (2001).

Classification:
- *Family.*—Balsaminaceae.
- *Botanical.*—*Impatiens* interspecific cross (*Impatiens hybrida* hort).
- *Common.*—*Impatiens.*
- *Designation.*—'SAKIMP027'.

Parentage:
- *Female parent.*—Proprietary *Impatiens* line 'NE-4391' (unpatented).
- *Male parent.*—Proprietary *Impatiens* line 'H-10UA' (unpatented).

Growth:
- *Time to produce a rooted cutting.*—About 4 weeks.
- *Environmental conditions for plant growth.*—The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2 to 3 days, 2 times in consecutive applications and then given one clear water application. Pots were top-dressed with a dry, slow release fertilizer containing 14% nitrogen, 14% phosphorus and 14% potassium. The typical average air temperature was 24° C. Time to bloom from propagation: 6 to 8 weeks.

Plant description:

*Habit.*—Compact.

*Life cycle.*—Tender perennial.

*Height* (*from soil line to top of foliage*).—18.0 cm.

*Spread.*—42.0 cm.

*Flowering requirements.*—Will flower so long as temperature is above 5° C.

*Temperature tolerances.*—Plants observed to continue flowering in a temperature range of 5° C. to 36° C. Plants can withstand high heat and humidity.

Branches:

*Number of branches.*—5 main branches, 13 branches total.

*Length of branches.*—Approximately 2.0 cm from soil line to first node, approximately 9.0 cm total.

*Diameter of branches.*—1.0 cm for the main branch.

*Color of branches.*—Closest to but lighter than RHS 146A (Yellow-Green).

Stems:

*General description.*—Strong; circular cross-section, smooth and shiny.

*Stem length.*—6.0 cm.

*Diameter.*—0.7 cm.

*Internode length.*—3.0 cm.

*Color.*—RHS 146A (Yellow-Green) with slight anthocyanin.

*Pubescence.*—Absent.

*Anthocyanin color.*—RHS 187B (Greyed-Purple).

Leaves:

*Arrangement.*—Whorled, with up to 5 leaves per node, opposite if only two leaves at one node.

*Shape.*—Lanceolate, curled.

*Apex.*—Acuminate.

*Base.*—Attenuate.

*Margin.*—Ciliate.

*Surface appearance* (*both surfaces*).—Dull, waxy.

*Surface pubescence* (*both surfaces*).—Absent.

*Length.*—8.5 cm.

*Width.*—3.5 cm.

*Color.*—Upper surface: Darker than but closet to RHS 147A (Yellow-Green). Lower surface: RHS 147B (Yellow-Green).

*Venation.*—Pinnate.

*Venation color* (*upper and lower surfaces*).—RHS 145C (Yellow-Green).

*Variegation.*—Absent.

*Fragrance.*—Absent.

*Petiole.*—Length: 1.0 cm. Diameter: 0.2 cm. Color: RHS 145C (Yellow-Green). Texture: Smooth, glabrous.

Flowers:

*Total number of flowers per node.*—1 to 3 in bloom, about 4 to 6 flower buds per node.

*Total number of flower per plant.*—Approximately 50 in bloom.

*Inflorescence type.*—Single flower with spur.

*Lastingness of individual blooms on the plant.*—14 days.

*Fragrance.*—Absent.

Flower bud:

*Surface texture.*—Glabrous.

*Length.*—2.0 cm.

*Diameter.*—1.5 cm.

*Shape.*—Deltoid, longitudinal cross-section.

*Color.*—RHS 155D (White) with RHS 143C (Green) at the edges.

Peduncle:

*Length.*—3.5 cm.

*Diameter.*—0.2 cm.

*Color.*—RHS 146A (Yellow-Green).

*Surface texture.*—Glabrous, smooth.

Corolla:

*Shape.*—Roughly circular with 5 radial petals.

*Diameter.*—Approximately 6.0 cm.

*Depth.*—1.0 cm.

*Petals.*—Shape: Obcordate. Apex: Emarginate (cleaved). Base: Attenuate. Margin: Entire. Pubescence (both surfaces): Glabrous. Length: 3.0 cm. Width: 3.4 cm. Color: Upper: Closest to RHS N155A (White). Lower: Closest to RHS N155A (White). Eye zone: Closest to RHS N155A (White).

Spur:

*Shape.*—Tubular; curved downward.

*Length.*—6.0 cm.

*Diameter.*—0.2 cm.

*Color.*—Closest to RHS N155A (White).

Calyx:

*Arrangement.*—Composed of 2 sepals.

*Sepals.*—Shape: Lanceolate. Apex: Caudate. Base: Subcordate. Margin: Entire. Surface texture: Glabrous. Color: RHS 145A (Yellow-Green). Length: 1.2 cm. Diameter: 0.8 mm.

Reproductive organs:

*Stamen number.*—Many.

*Stamen form.*—Fused; split into 4 lobes.

*Filament length.*—0.6 cm.

*Filament color.*—RHS 36A (Red).

*Anther length.*—0.5 cm.

*Anther color.*—RHS 155A (White).

*Pollen color.*—RHS 155D (White).

*Pollen amount.*—Abundant.

*Pollen description.*—Powdery.

*Ovary arrangment.*—Parietal.

*Ovary surface color.*—RHS 145A (Yellow-Green).

*Pistil number.*—5.

*Stigma color.*—RHS 143A (Green).

*Style length.*—0.6 cm.

*Style color.*—RHS 143A (Green).

*Seed production.*—Absent.

Disease and insect resistance: No particular resistance or susceptibility observed.

COMPARISON WITH PARENTAL LINES AND KNOWN VARIETY

'SAKIMP027' is a new and unique variety of *Impatiens* owing to its white flower color, strong root system and a compact plant growth habit. 'SAKIMP027' is distinguished from its parents mainly by flower color as shown in Table 1 below:

TABLE 1

Comparison with Parental Lines

| Characteristic | 'SAKIMP027' | Female Parent 'NE-4391' | Male Parent 'H-10UA' |
|---|---|---|---|
| Flower color | White | Pinkish-white | White |
| Plant habit | Compact | Less compact than 'SAKIMP027' | More compact than 'SAKIMP027' |
| Flower size | Large | Medium | Extra-large |
| Leaf variegation | Absent | Present | Absent |

'SAKIMP027' is a new and unique variety of *Impatiens* owing to its white flower color, strong root system and a compact plant growth habit. 'SAKIMP027' is most similar to the commercial *Impatiens* variety 'SAKIMP010' (U.S. Plant Pat. No. 19,616), commercially known as SunPatiens® 'Vigorous White Improved'; however there are differences as described in the table below.

TABLE 2

Comparison with Similar Variety

| Characteristic | 'SAKIMP027' | 'SAKIMP010' |
|---|---|---|
| Petal color, upper surface | RHS N155A (White) | RHS N155B (White) |
| Petal color, lower surface | RHS N155A (White) | RHS N155B (White) |
| Plant habit | Compact | Vigorous |

We claim:

1. A new and distinct cultivar of New Guinea *Impatiens* plant as shown and described herein.

* * * * *